United States Patent
Hua et al.

(10) Patent No.: US 11,964,096 B2
(45) Date of Patent: Apr. 23, 2024

(54) INTEGRATED SEALED MICRO-MESH NEBULIZATION MODULE

(71) Applicant: Feellife Health INC., Shenzhen (CN)

(72) Inventors: Jian Hua, Guangdong (CN); Xuefeng Song, Guangdong (CN)

(73) Assignee: Feellife Health INC., Shenzhen (CN)

( * ) Notice: Subject to any disclaimer, the term of this patent is extended or adjusted under 35 U.S.C. 154(b) by 870 days.

(21) Appl. No.: 15/733,489

(22) PCT Filed: Jun. 26, 2018

(86) PCT No.: PCT/CN2018/092923
§ 371 (c)(1),
(2) Date: Aug. 10, 2020

(87) PCT Pub. No.: WO2019/218428
PCT Pub. Date: Nov. 21, 2019

(65) Prior Publication Data
US 2020/0368455 A1    Nov. 26, 2020

(30) Foreign Application Priority Data
May 18, 2018 (CN) .......................... 201820743644.3

(51) Int. Cl.
*A61M 11/00* (2006.01)
(52) U.S. Cl.
CPC .................................. *A61M 11/005* (2013.01)
(58) Field of Classification Search
CPC .............. A61M 11/005; A61M 15/001; A61M 15/0085
See application file for complete search history.

(56) References Cited

U.S. PATENT DOCUMENTS

| | | | |
|---|---|---|---|
| 2005/0081844 | A1 | 4/2005 | Grychowski et al. |
| 2006/0207591 | A1 | 9/2006 | Gallem et al. |

(Continued)

FOREIGN PATENT DOCUMENTS

| | | | |
|---|---|---|---|
| CN | 206934411 | A1 | 4/2005 |
| CN | 2905087 | Y | 5/2007 |
| CN | 103041480 | A | 4/2013 |
| CN | 203749956 | U | 8/2014 |

(Continued)

OTHER PUBLICATIONS

ISA/CN, PCT International Search Report and Written Opinion dated Feb. 19, 2019 issued in PCT International Application No. PCT/CN2018/092923.

(Continued)

*Primary Examiner* — Rachel T Sippel
(74) *Attorney, Agent, or Firm* — Gottlieb, Rackman & Reisman, PC

(57) ABSTRACT

Disclosed is an integrated sealed micro-mesh nebulization module, which includes: an nebulization device and a nozzle mechanism disposed on the nebulization device, the nozzle mechanism disposed on the nebulization device is detachably connected with the nebulization device; the nebulization module comprises an annular base, a lower shell disposed in the annular base, an upper shell disposed on the lower shell, a micro-mesh nebulization sheet disposed on the lower shell, a first sealing ring and a second sealing ring respectively disposed on both sides of the micro-mesh nebulization sheet, and a metal contact disposed between the lower shell and the upper shell, with one end connected with the micro-mesh nebulization sheet through a wire, and the other end extending to an exterior of the lower shell and connected with an external driving circuit.

4 Claims, 9 Drawing Sheets

Flowing direction of gas

(56) References Cited

U.S. PATENT DOCUMENTS

| | | | |
|---|---|---|---|
| 2007/0267010 A1 | 11/2007 | Fink et al. | |
| 2008/0299049 A1* | 12/2008 | Stangl | A61M 15/0086 128/200.14 |
| 2013/0239956 A1* | 9/2013 | Schulz | A61M 15/0085 128/200.14 |
| 2015/0102124 A1 | 4/2015 | Hu et al. | |
| 2015/0238993 A1 | 8/2015 | Hsieh et al. | |
| 2015/0306334 A1 | 10/2015 | Gallem et al. | |
| 2016/0022927 A1 | 1/2016 | Tsai et al. | |
| 2016/0022929 A1* | 1/2016 | Cheng | A61M 15/0025 128/200.16 |
| 2018/0272079 A1* | 9/2018 | Porter | A61M 11/001 |
| 2018/0318530 A1* | 11/2018 | Liu | A24F 40/40 |
| 2019/0247599 A1* | 8/2019 | Lee | A61M 16/0006 |
| 2020/0069891 A1* | 3/2020 | Gupta | A61M 15/0066 |

FOREIGN PATENT DOCUMENTS

| | | |
|---|---|---|
| CN | 105311718 A | 2/2016 |
| CN | 205181935 U | 4/2016 |
| CN | 205198620 U | 5/2016 |
| CN | 205198623 U | 5/2016 |
| CN | 106178202 A | 12/2016 |
| CN | 206167548 U | 5/2017 |
| CN | 107913819 A | 4/2018 |

OTHER PUBLICATIONS

Extended European Search Report for PCT/CN2018092923, dated Oct. 18, 2021, 10 pages.

Evaluation Report of Utility Model Patent for Chinese Patent ZL2018207436443, dated Feb. 16, 2022, 6 pages.

* cited by examiner

Flowing direction of gas

INTEGRATED SEALED MICRO-MESH NEBULIZATION MODULE

CROSS-REFERENCE TO RELATED APPLICATIONS

This application is a national stage filing under 35 U.S.C. § 371 of international application number PCT/CN2018/092923, filed Jun. 26, 2018, which claims priority to Chinese patent application No. 201820743644.3 filed May 18, 2018. The contents of these applications are incorporated herein by reference in their entirety.

TECHNICAL FIELD

The present invention belongs to the field of electronic nebulizers, and more particularly, relates to an integrated sealed micro-mesh nebulization module.

BACKGROUND

Nebulizer treatment has a principle of nebulizing a medicine into micro droplets, and the atomized liquid is inhaled into a human body by respiration to achieve a therapeutic effect. In this way, not only pain of taking the medicine is alleviated, but also waste of the medicine caused by a process of taking the medicine is avoided, and the therapeutic effect of the medicine is also able to be fully exerted. A nebulizer has many functions in medical treatment, comprising anti-inflammation, cough relief, phlegm elimination, bronchospasm relief, smoothing of airway and improvement of ventilation, so that a patient may not feel dyspnea during treatment. The nebulizer may also be used before and after chest surgery to prevent respiratory tract infection, so that the surgery may have good a result, and the nebulizer may be used in treatment of lung cancer with an anticancer medicine. A micro-mesh nebulization sheet is an important part of a micro-mesh nebulizer, which is mainly made of a metal mesh and a ceramic material. The micro-mesh nebulization sheet oscillates at a certain frequency under driving of a circuit, so that a ceramic vibrating reed oscillates resonantly, thus driving the metal mesh to oscillate at a high speed. Therefore, a liquid medicine passes through numerous micro-mesh openings in the metal mesh and is quickly ejected to form countless atomized micro particles. However, the nebulization sheet in the market now usually needs to be purchased separately, and a series of problems such as clamping and fixing, sealing and waterproofing, circuit welding and so on may be encountered during assembly, thus greatly affecting a universality of the nebulization sheet. If the nebulization sheet needs to be disassembled, such as cleaning and sterilization, a nozzle and other connecting parts must be disassembled before performing routine maintenance on the nebulizer.

SUMMARY

In view of the above problem, the present invention is intended to provide an integrated sealed micro-mesh nebulization module, which is universal and convenient to mount, and facilitates sterilization and cleaning.

In order to achieve the above objective, the present invention provides an integrated sealed micro-mesh nebulization module, which comprises a nebulization device and a nozzle mechanism disposed on the nebulization device, wherein the nebulization device is detachably connected with the nozzle mechanism disposed on the nebulization device. The nebulization module comprises an annular base, a lower shell disposed in the annular base, an upper shell disposed on the lower shell, a micro-mesh nebulization sheet disposed on the lower shell, a first sealing ring and a second sealing ring respectively disposed on both sides of the micro-mesh nebulization sheet, and a metal contact disposed between the lower shell and the upper shell, with one end connected with the micro-mesh nebulization sheet through a wire, and the other end extending to an exterior of the lower shell and connected with an external driving circuit. A first through hole is disposed in a center of the upper shell, and a second through hole corresponding to the first through hole is disposed in a center of the lower shell. The nozzle mechanism comprises a bottom cover disposed on one side of the upper shell in the annular base, a tubular spout disposed on the bottom cover, and gas outlets for discharging excess atomized gas respectively disposed on the bottom cover at upper and lower sides of the spout. The bottom cover is provided with a central hole corresponding to the first through hole. Therefore, the upper shell, the first sealing ring, the micro-mesh nebulization sheet, the second sealing ring and the lower shell are connected in sequence to form a sealed and closed state, so that gas generated by liquid flowing through the second through hole on the micro-mesh nebulization sheet may be sprayed out from the spout through the first through hole and the central hole in sequence, and excess gas is discharged from the gas outlet. In addition, an I-shaped sealing ring is used as the second sealing ring.

In some embodiments, an edge of the upper shell is provided with an annular bulge serving as an ultrasonic line.

In some embodiments, the lower shell is provided with a first threaded hole and a second threaded hole for connecting the bottom cover.

In some embodiments, the gas outlet is an arc-shaped port, and a shielding portion is disposed at an edge of the port for discharging gas inside the spout and preventing an external foreign matter from entering the spout. Therefore, not only the atomized gas generated inside the spout may be discharged to the outside from the gas outlet, but also the external foreign matter may be prevented from entering the spout to cause pollution through this hidden-type design.

In some embodiments, a first gas channel is further provided at an inner wall of the spout, the nebulization device is also provided with a second gas channel corresponding to the first gas channel, and the first gas channel is communicated with the second gas channel.

In some embodiments, a limiting groove and a limiting bulge are respectively provided at a contact surface between the upper shell and the lower shell.

The present invention has the beneficial effects of being universal and convenient to mount, and facilitating sterilization and cleaning. Since the upper shell, the first sealing ring, the micro-mesh nebulization sheet, the second sealing ring and the lower shell are connected, extruded and fixed together in sequence by ultrasonic welding, the micro-mesh nebulization sheet is electrically connected with the metal contact, and the metal contact is externally connected with the driving circuit, so that the micro-mesh nebulization sheet and the components thereof are modularized to form a nebulizing unit, thus improving a universality of the nebulization sheet. Moreover, an extension portion of the lower shell is provided with the first threaded hole for connecting the nebulizing unit with the nozzle; the bottom cover of the nozzle is provided with the second threaded hole for connecting the nozzle with a nebulizer body; and the gas outlet is disposed at an adjacent position between the spout and the bottom cover for discharging the excess atomized gas. In this way, the nebulizing unit is mounted on the nozzle to form the integrated nebulization module, and then the nebulization module is mounted on the nebulizer body, so that the nebulizing unit can be disassembled by disassembling the nozzle, thus facilitating cleaning and sterilization of the nebulization sheet. In addition, the I-shaped sealing ring is used as the second sealing ring, so that the corresponding sealing ring can be omitted at a contact portion between the lower shell of the nebulizing unit and the nebulizer body, and a structure of a joint among the components is simpler while being waterproof, so as to prevent misplacement, dropping, loss and so on of the parts. Therefore, the present invention not only improves the universality of the nebulization sheet, but also can disassemble the nebulizing unit by disassembling the nozzle, thus further facilitating cleaning and sterilization of the nebulization sheet.

DETAILED DESCRIPTION

The present invention is further described in detail hereinafter with reference to the accompanying drawings.

Embodiment 1

Figure 1:
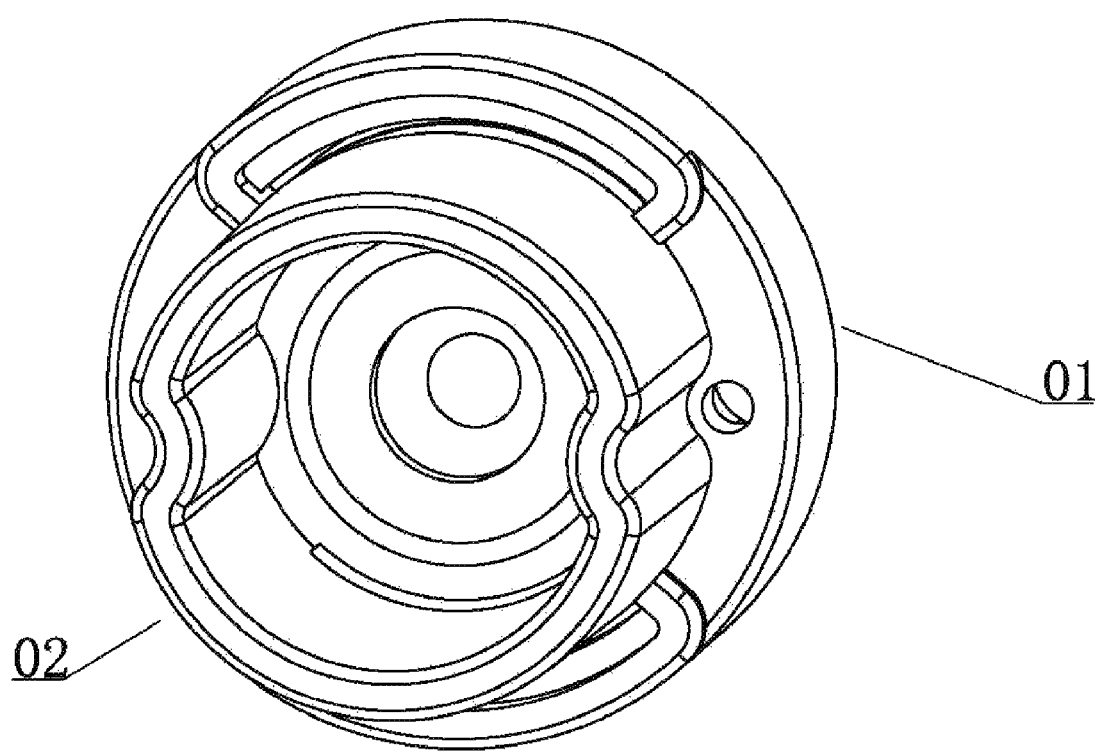
FIG. 1 is a structure diagram of the embodiment 1.
Figure 2:
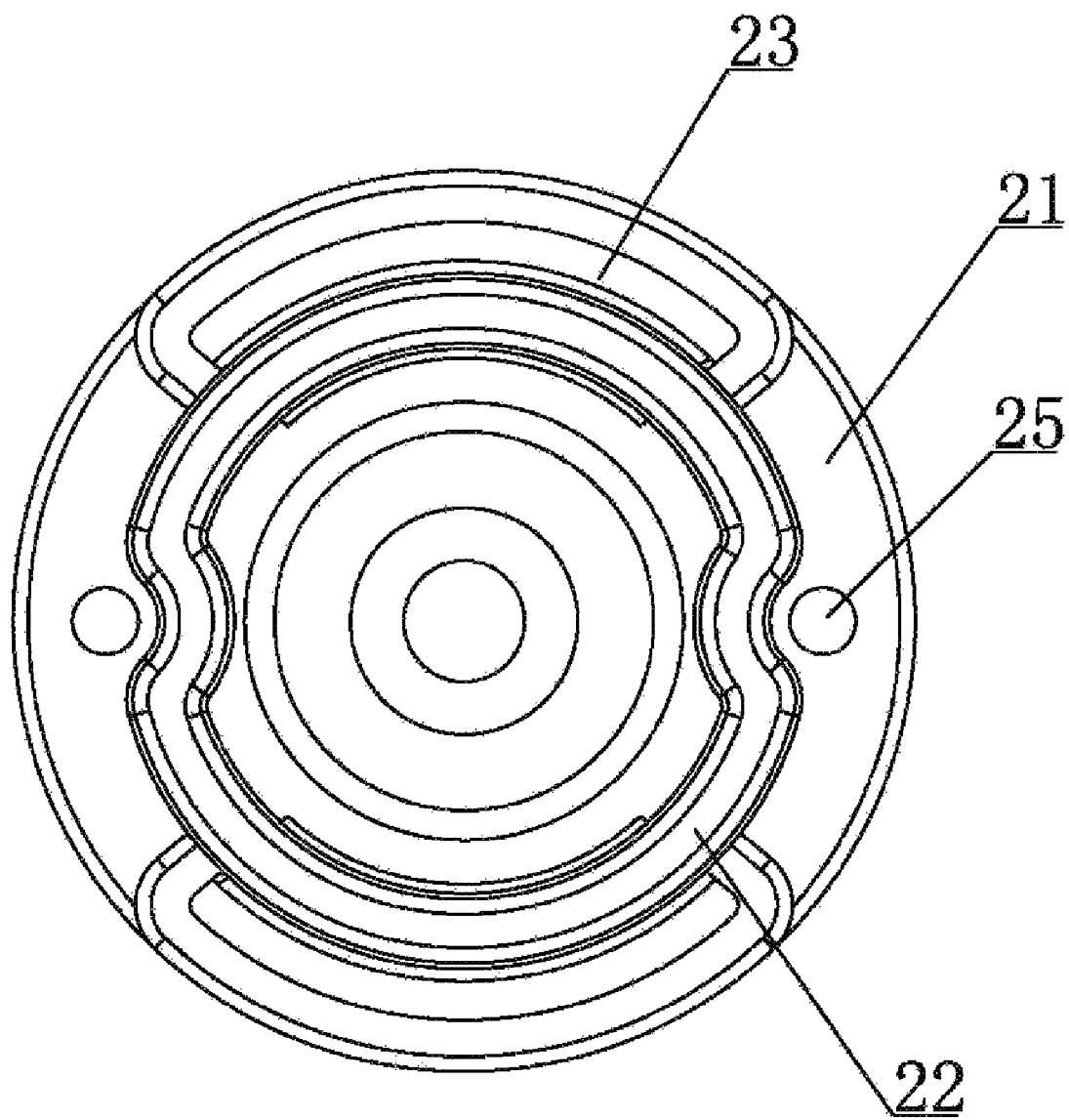
FIG. 2 is a structure diagram of a front view of the embodiment 1.
Figure 3:
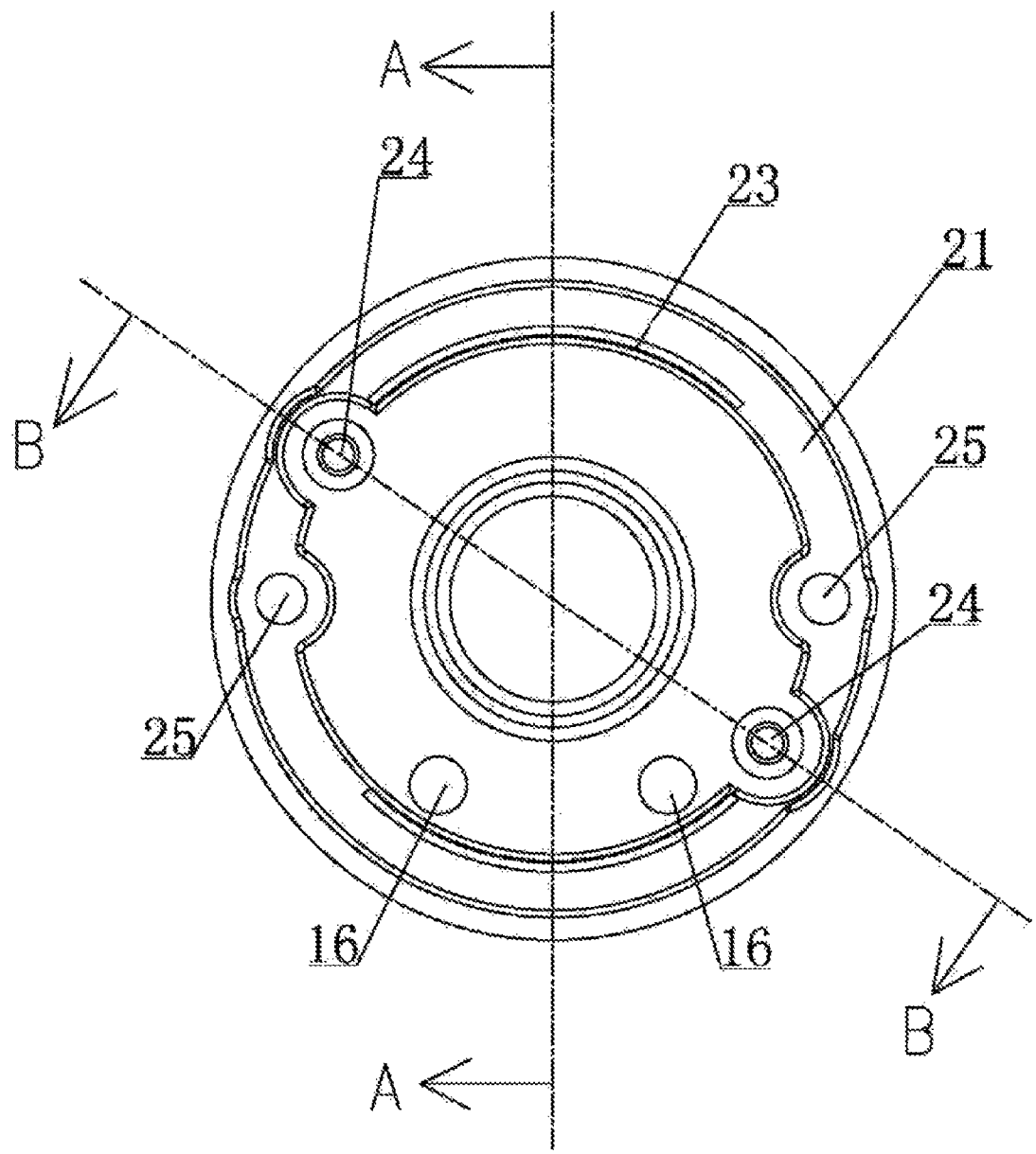
FIG. 3 is a structure diagram of a rear view of the embodiment 1.
Figure 4:
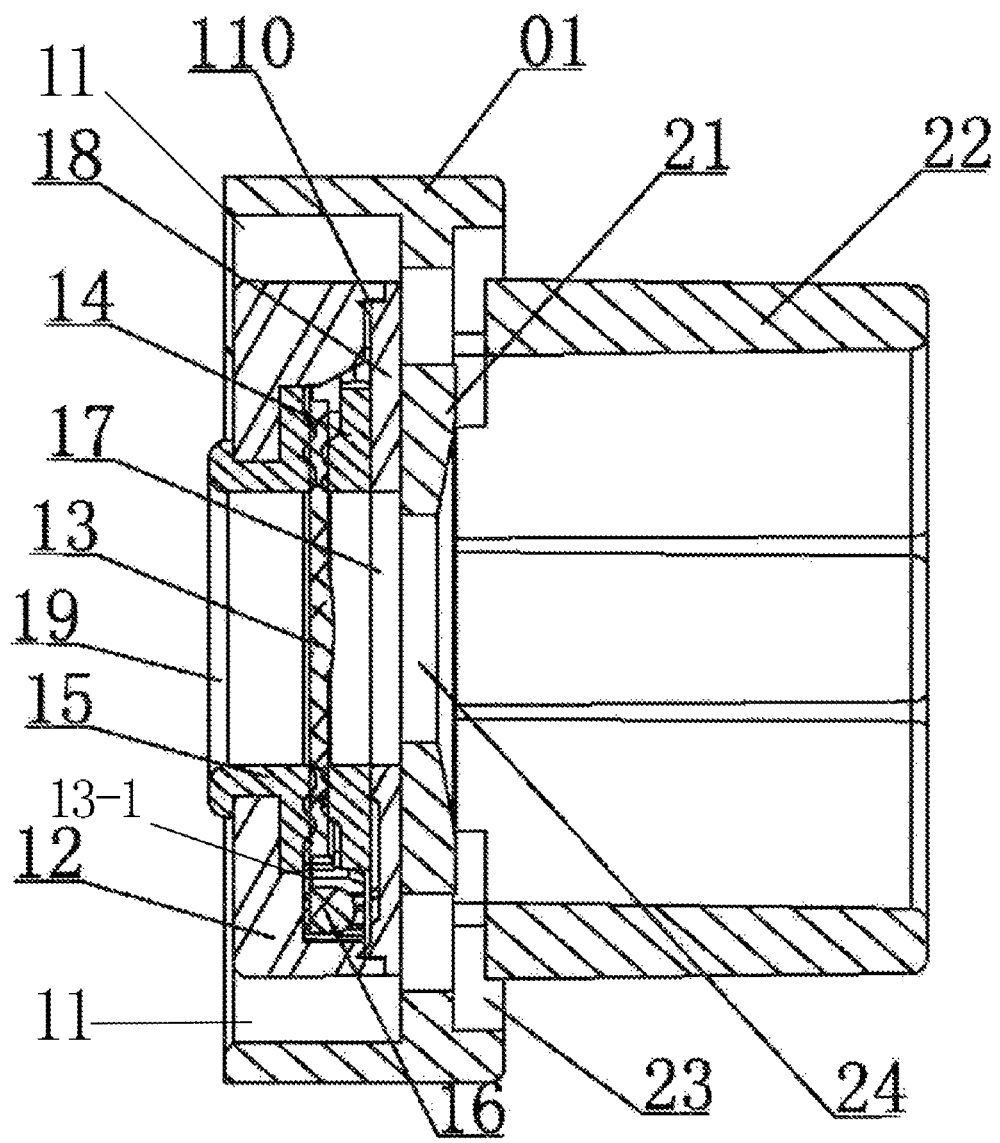
FIG. 4 is a structure diagram of an A-A cross-section in FIG. 2.
Figure 5:
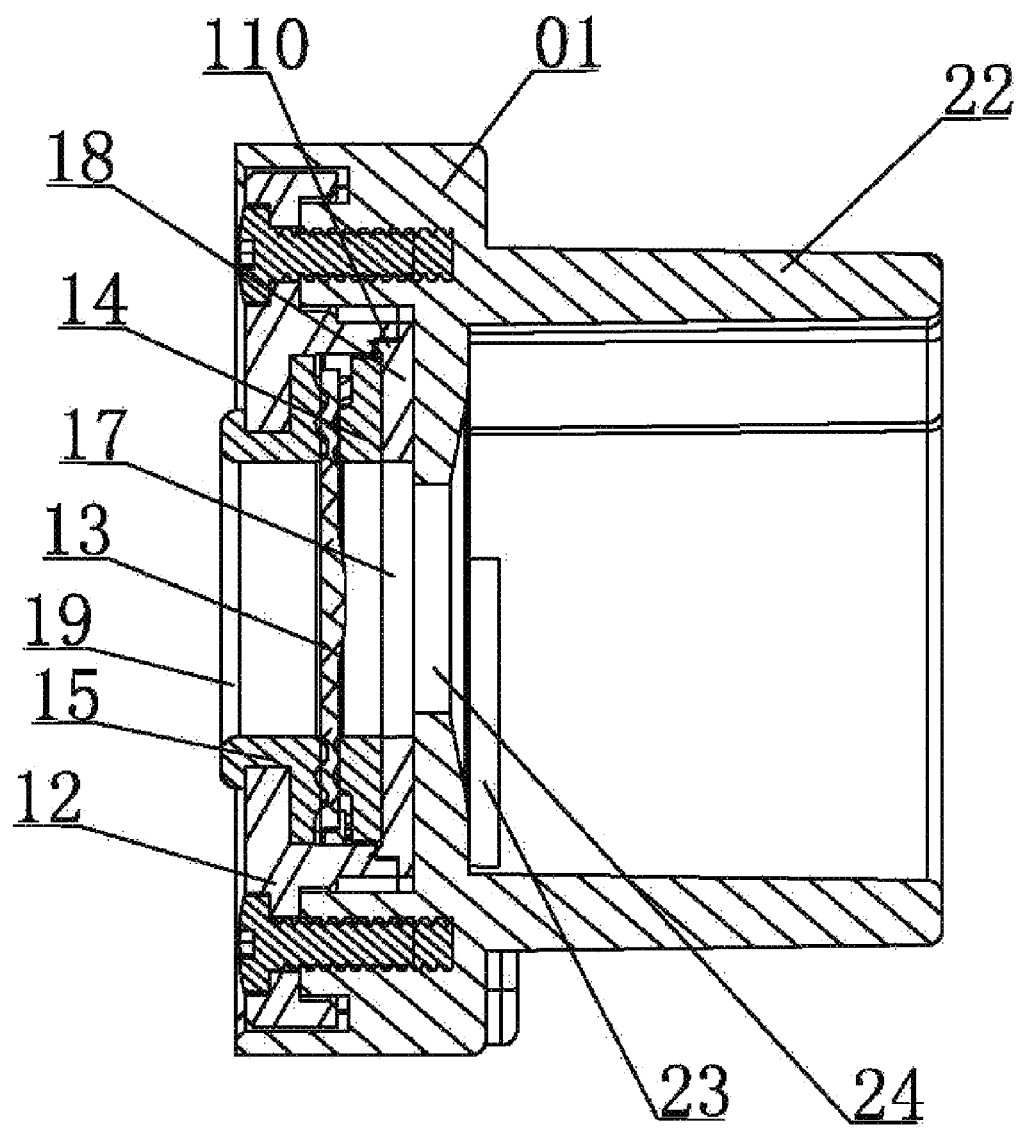
FIG. 5 is a structure diagram of a B-B cross-section in FIG. 2.

As shown in FIG. 1 to FIG. 5, an integrated sealed micro-mesh nebulization module comprises a nebulization device 01 and a nozzle mechanism 02 disposed on the nebulization device 01. The nebulization device 01 is detachably connected with the nozzle mechanism 02 disposed on the nebulization device 01. The nebulization device 01 comprises an annular base 11, a lower shell 12 disposed in the annular base 11, an upper shell 18 disposed on the lower shell 12, a micro-mesh nebulization sheet 13 disposed on the lower shell 12, a first sealing ring 14 and a second sealing ring 15 respectively disposed on both sides of the micro-mesh nebulization sheet 13, and a metal contact 16 disposed between the lower shell 12 and the upper shell 18, with one end connected with the micro-mesh nebulization sheet 13 through a wire 13-1, and the other end extending to an exterior of the lower shell 12 and connected with an external driving circuit. A first through hole 17 is disposed in a center of the upper shell 18, and a second through hole 19 corresponding to the first through hole 17 is disposed in a center of the lower shell 12. The nozzle mechanism 02 comprises a bottom cover 21 disposed on one side of the upper shell 18 in the annular base 11, a tubular spout 22 disposed on the bottom cover 21, and gas outlets 23 for discharging excess atomized gas respectively disposed on the bottom cover 21 at upper and lower sides of the spout 22. The bottom cover 21 is provided with a central hole corresponding to the first through hole 17, this central hole is first threaded hole 24. The upper shell 18, the first sealing ring 14, the micro-mesh nebulization sheet 13, the second sealing ring 15 and the lower shell 12 are connected in sequence to form a sealed and closed state, so that gas generated by liquid flowing through the second through hole 19 on the micro-mesh nebulization sheet 13 may be sprayed out from the spout 22 through the first through hole 17 and the first threaded hole 24 in sequence, and excess gas is discharged from the gas outlet 23. In addition, an I-shaped sealing ring is used as the second sealing ring 15. The above spout 22 may have various shapes with a hollow interior. On the basis of making the spout 22 into a cylinder, an inwardly concave arc is designed at a corresponding position. The gas outlet may also be disposed at any position outside a wall of the spout 22 or at any adjacent position of the spout 22 and the bottom cover 21, and may have various shapes. An edge of the upper shell 18 is provided with an annular bulge 110 serving as an ultrasonic line 110. The lower shell 12 is provided with first threaded holes 24 and second threaded holes 25 for connecting the bottom cover 21. The gas outlet 23 is an arc-shaped opening, and a convex shielding portion is disposed at the edge of the gas outlet 23 to shield the gas outlet 23. Not only the atomized gas generated inside the spout may be discharged to the outside from the gas outlet 23, but also the external foreign matter may be prevented from entering the spout to cause pollution through this hidden design. A limiting groove and a limiting bulge are respectively provided at a contact surface between the upper shell 18 and the lower shell 12, thus being closed more tightly.

During application, the upper shell 18, the first sealing ring 14, the micro-mesh nebulization sheet 13, the second sealing ring 15 and the lower shell 12 are connected, extruded and fixed together in sequence by ultrasonic welding, the micro-mesh nebulization sheet 13 is electrically connected with the metal contact 16, and the metal contact 16 is externally connected with the driving circuit, so that the micro-mesh nebulization sheet 13 and the components thereof are modularized to form a nebulizing unit, thus improving a use universality of the nebulization sheet. Moreover, an extension portion of the lower shell 12 is provided with the first threaded holes 24 for connecting the nebulizing unit with the nozzle. The bottom cover 21 of the nozzle is provided with the second threaded holes 25 for connecting the nozzle with a nebulizer body. The gas outlet 23 is disposed at an adjacent position between the spout 22 and the bottom cover 21 for discharging the excess atomized gas. In this way, the nebulizing unit is mounted on the nozzle to form the integrated nebulization module, and then the nebulization module is mounted on the nebulizer body, so that the nebulizing unit may be disassembled by disassembling the nozzle, thus facilitating cleaning and sterilization of the nebulization sheet. In addition, the I-shaped sealing ring is used as the second sealing ring 15, so that the corresponding sealing ring may be omitted at a contact portion between the lower shell 12 of the nebulizing unit and the nebulizer body, and a structure of a joint among the components is simpler while being waterproof, so as to prevent misplacement, dropping, loss and so on of the parts.

Embodiment 2

Figure 6:
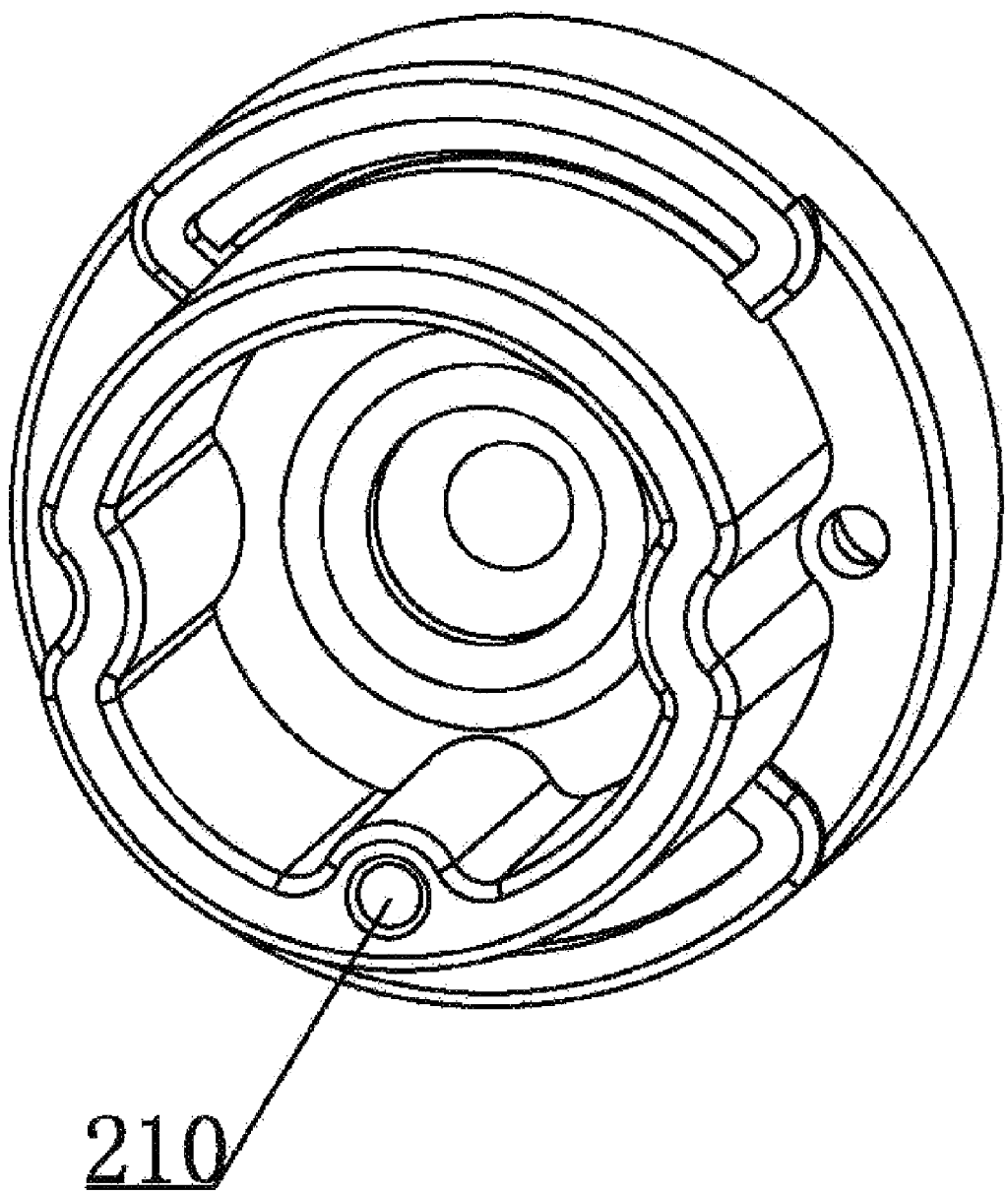
FIG. 6 is a structure diagram of the embodiment 2.
Figure 7:
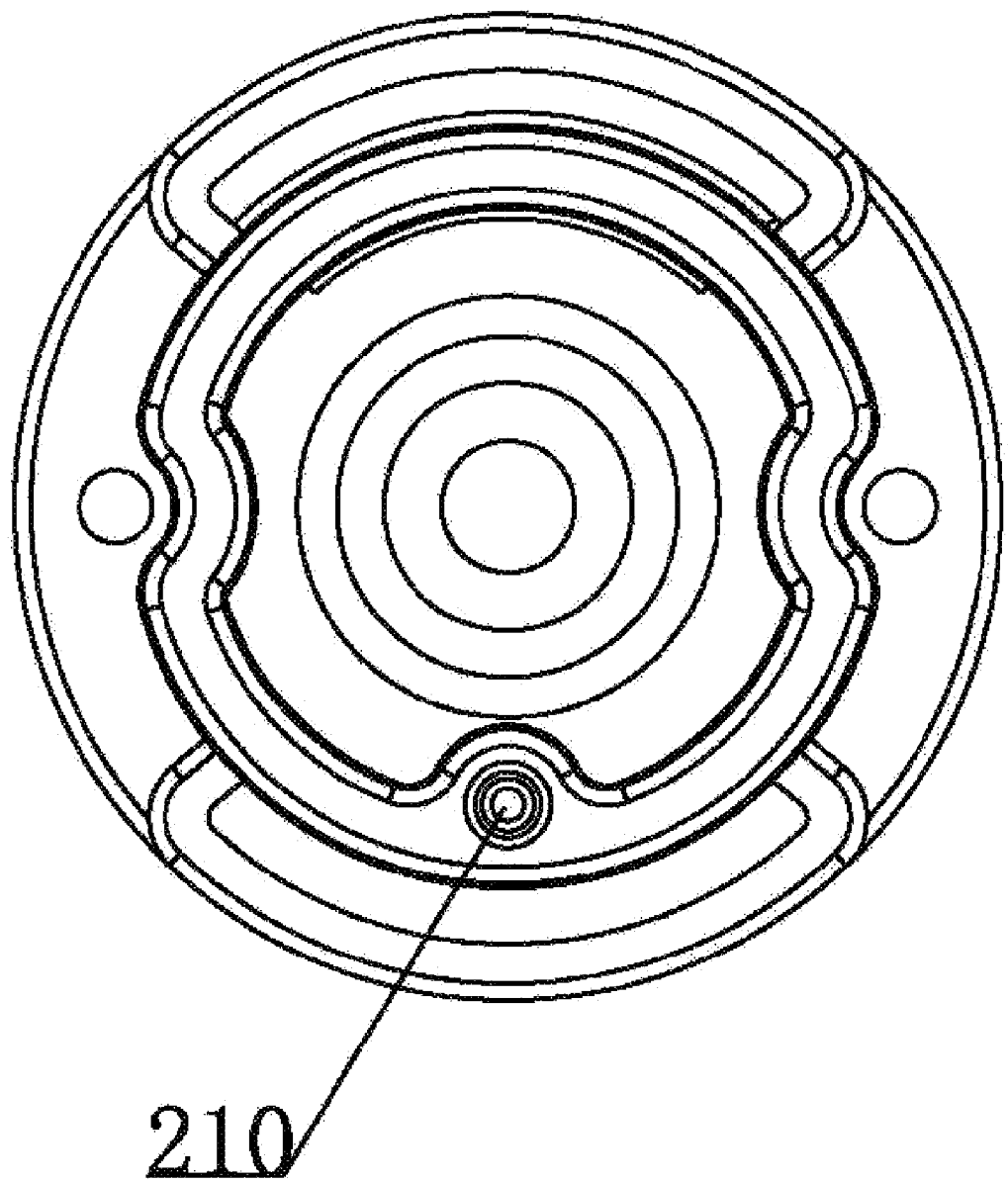
FIG. 7 is a structure diagram of a front view of the embodiment 2.
Figure 8:
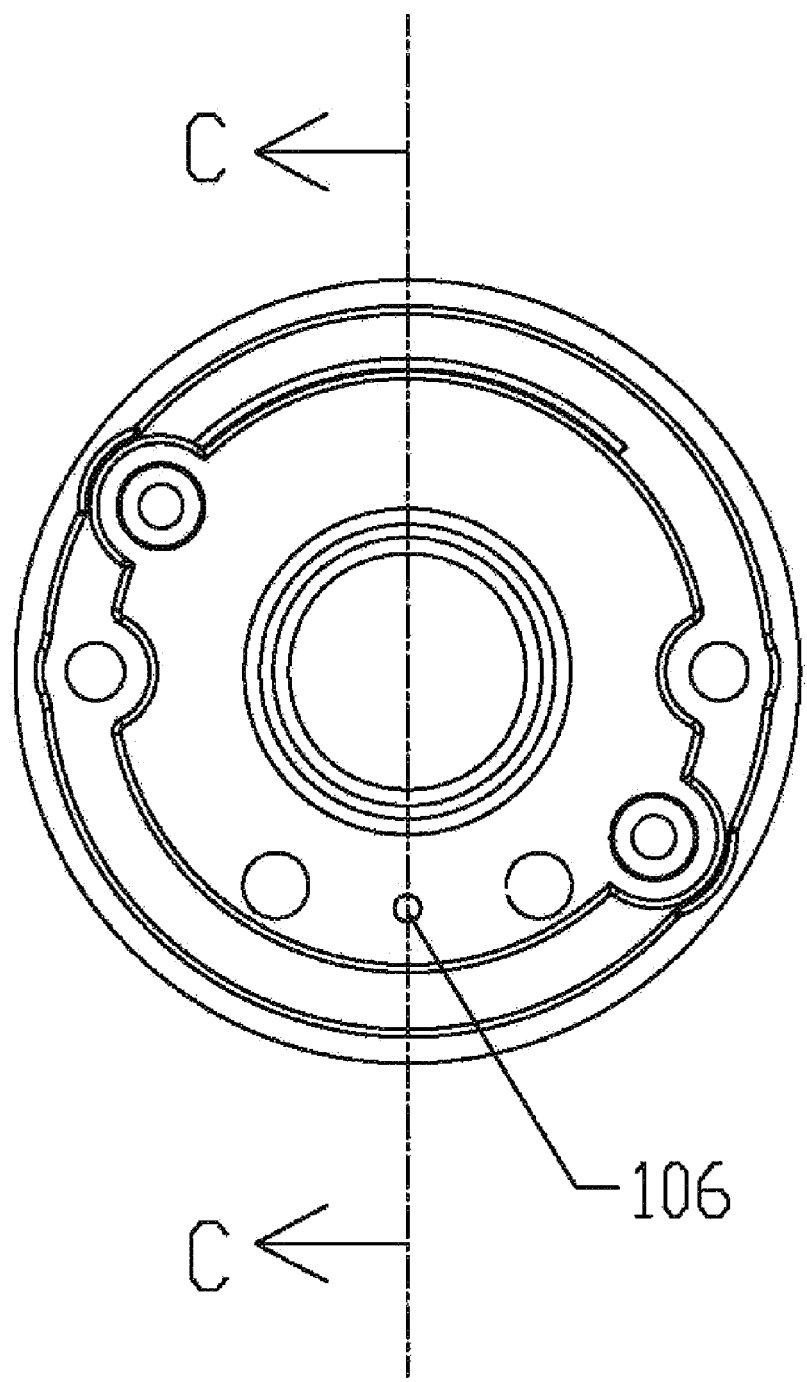
FIG. 8 is a structure diagram of a rear view of the embodiment 2.
Figure 9:
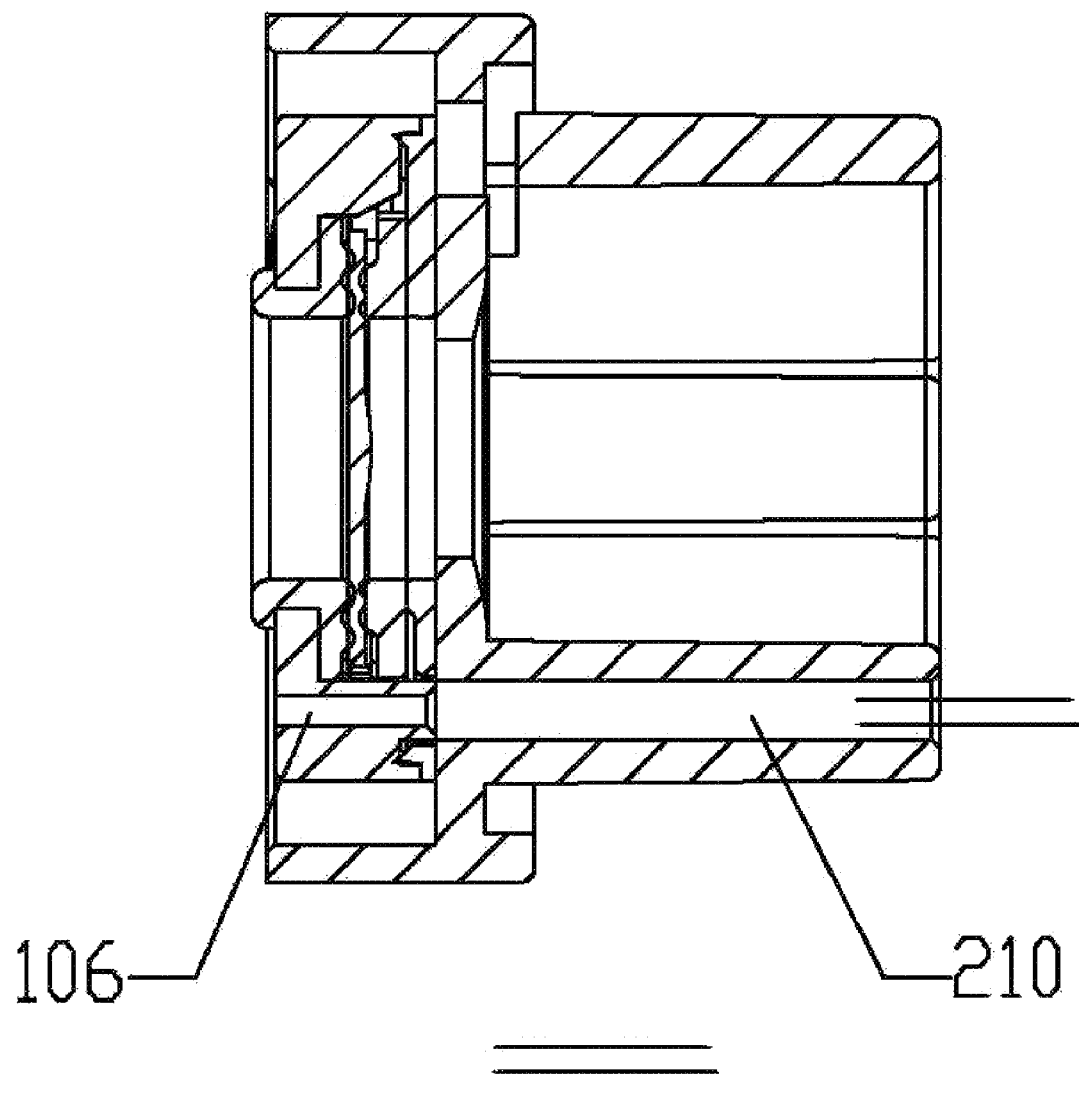
FIG. 9 is a structure diagram of a C-C cross-section in FIG. 8.

As shown in FIG. 6 to FIG. 9, an integrated sealed micro-mesh nebulization module is added with a first gas channel 210 on an inner wall of a spout 22 on the basis of a structure of the embodiment 1. The first gas channel 210 may be disposed at any position on the inner wall of the spout 22. In the embodiment 2, the first gas channel 210 is disposed at a central line of a bottom portion of the inner wall. Correspondingly, the nebulization device 01 is provided with a second gas channel 106 corresponding to the first gas channel 210, and the second gas channel 106 is formed by perforated portions of moulds of an upper shell 18 and a lower shell 12. The second gas channel 106 is communicated with the first gas channel 210, and provides an independent gas channel for the nebulization module, so that an air flow generated by expiration and inspiration of a user is not interfered by nebulization of a nebulizer, thus being convenient for detecting a pressure and/or a flow rate of the air flow respired by the user. In the embodiment, since a nozzle mechanism 02 is added with the first gas channel 210, a gas outlet 23 below the spout 22 is omitted. Since the nebulization device 01 is provided with the second gas channel 106, sizes of components such as a micro-mesh nebulization sheet and a sealing ring are adjusted.

The above embodiments are only some embodiments of the present invention. Those of ordinary skills in the art may further make several modifications and improvements without departing from the inventive concept of the present invention. In particular, the position of the gas channel may be designed to other places of the shell. These modifications and improvements all fall within the scope of protection of the present invention.

What is claimed is:

1. An integrated sealed micro-mesh nebulization module, comprising:
   a nebulization device and a nozzle mechanism disposed on the nebulization device, wherein the nozzle mechanism disposed on the nebulization device is detachably connected with the nebulization device;
   wherein the nebulization device comprises an annular base, a lower shell disposed in the annular base, an upper shell disposed on the lower shell, a micro-mesh nebulization sheet disposed on the lower shell, a first sealing ring and a second sealing ring respectively disposed on both sides of the micro-mesh nebulization sheet, and a metal contact disposed between the lower shell and the upper shell, with one end of the metal contact connected with the micro-mesh nebulization sheet through a wire, and the other end of the metal contact extending to an exterior of the lower shell;
   wherein a first through hole is disposed in a center of the upper shell, and a second through hole corresponding to the first through hole is disposed in a center of the lower shell; and
   wherein the nozzle mechanism comprises a bottom cover disposed on one side of the upper shell in the annular base, a tubular spout disposed on the bottom cover, and gas outlets for discharging excess atomized gas respectively disposed on the bottom cover at upper and lower sides of the spout; and wherein the bottom cover is provided with a central hole corresponding to the first through hole,
   wherein a first gas channel is further provided at an inner wall of the spout, the nebulization device is further provided with a second gas channel corresponding to the first gas channel, and the first gas channel is communicated with the second gas channel.

2. The integrated sealed micro-mesh nebulization module of claim 1, wherein an edge of the upper shell is provided with an annular bulge.

3. The integrated sealed micro-mesh nebulization module of claim 2, wherein the lower shell is provided with a first threaded hole and a second threaded hole for connecting the bottom cover.

4. The integrated sealed micro-mesh nebulization module of claim 1, wherein a limiting groove and a limiting bulge are respectively provided at a contact surface between the upper shell and the lower shell.

* * * * *